United States Patent [19]

Moorehead et al.

[11] Patent Number: 5,205,834
[45] Date of Patent: * Apr. 27, 1993

[54] TWO-WAY OUTDWELLING SLIT VALVING OF MEDICAL LIQUID FLOW THROUGH A CANNULA AND METHODS

[76] Inventors: H. Robert Moorehead, 1694 E. 5685 South, Salt Lake City, Utah 84121; Thomas A. Wiita, 1127 Goldenrod, Corona del Mar, Calif. 92625

[ * ] Notice: The portion of the term of this patent subsequent to Feb. 18, 2009 has been disclaimed.

[21] Appl. No.: 903,410

[22] Filed: Jun. 24, 1992

Related U.S. Application Data

[63] Continuation of Ser. No. 776,927, Oct. 15, 1991, Pat. No. 5,169,393, which is a continuation of Ser. No. 577,941, Sep. 4, 1990.

[51] Int. Cl.⁵ .............................................. A61M 5/00
[52] U.S. Cl. .................................... 604/247; 604/257; 137/493.9; 137/512.4; 137/845
[58] Field of Search ................ 604/30, 31, 167, 246, 604/247, 257; 137/493, 493.1, 493.8, 493.9, 512.4, 843-845, 859

[56] References Cited

U.S. PATENT DOCUMENTS

| | | |
|---|---|---|
| 274,447 | 3/1883 | Kennish . |
| 703,101 | 6/1902 | Ware . |
| 996,588 | 6/1911 | Kennedy . |
| 1,367,793 | 2/1921 | Blair . |
| 2,069,105 | 1/1937 | Engle . |
| 2,629,393 | 2/1953 | Langdon ............................. 137/217 |
| 2,793,649 | 5/1957 | Hamer ................................ 137/204 |
| 2,941,544 | 6/1960 | Peras .................................. 137/525 |
| 2,969,066 | 1/1961 | Holter et al. . |
| 3,007,527 | 11/1961 | Nelson ................................ 166/225 |
| 3,020,913 | 2/1962 | Heyer . |
| 3,111,125 | 11/1963 | Schulte . |
| 3,566,875 | 3/1971 | Stoehr ................................ 128/350 |
| 3,620,500 | 11/1971 | Santomieri ....................... 251/149.1 |
| 3,654,932 | 4/1972 | Newkirk et al. . |
| 3,662,955 | 5/1972 | Takanashi ......................... 239/145 |
| 3,811,466 | 5/1974 | Ohringer ........................... 137/493 |
| 3,865,236 | 2/1975 | Rycroft .............................. 206/364 |
| 3,885,561 | 5/1975 | Cami . |
| 3,888,249 | 6/1975 | Spencer . |
| 3,899,135 | 8/1975 | O'Brian ............................. 239/534 |
| 4,084,606 | 4/1978 | Mittleman ........................ 137/102 |
| 4,141,379 | 2/1979 | Manske ............................ 137/496 |
| 4,143,853 | 3/1979 | Abramson ....................... 251/149.1 |
| 4,178,643 | 12/1979 | Cox, Jr. ............................... 3/36 |
| 4,327,722 | 5/1982 | Groshong ........................ 604/170 |
| 4,341,239 | 7/1982 | Atkinson .......................... 137/493 |
| 4,381,591 | 5/1983 | Barger et al. .................... 29/157.1 R |
| 4,387,879 | 6/1983 | Tauschinski ..................... 251/149.1 |
| 4,430,081 | 2/1984 | Timmermans .................. 604/256 |
| 4,431,426 | 2/1984 | Groshong et al. .............. 604/280 |
| 4,434,810 | 3/1984 | Atkinson .......................... 137/493 |
| 4,475,898 | 10/1984 | Brodner et al. ................. 604/9 |

(List continued on next page.)

FOREIGN PATENT DOCUMENTS

| | | |
|---|---|---|
| 737249 | 6/1966 | Canada .............................. 604/247 |
| 0370721 | 11/1989 | European Pat. Off. . |
| 145824 | 2/1961 | U.S.S.R. . |
| 1417013 | 12/1975 | United Kingdom . |
| 1557504 | 12/1977 | United Kingdom . |
| 2065479 | 12/1980 | United Kingdom . |
| 2217433 | 10/1989 | United Kingdom .............. 604/247 |

Primary Examiner—John D. Yasko
Assistant Examiner—Anthony Gutowski
Attorney, Agent, or Firm—Lynn G. Foster

[57] ABSTRACT

A cardiovascular outdwelling, normally closed, pressure-responsive slit valve liquid flow control and related methods wherein a diaphragm having a slit therein is flexed distally by hydrostatic pressure and proximally by negative pressure at different points in time to selectively open the slit and accommodate the flow of IV solution to a medical patient through a cannula and blood sampling from the cardiovascular system of the patient through the cannula in such a way as to prevent bleed-back and clotting of blood within the cannula.

24 Claims, 2 Drawing Sheets

U.S. PATENT DOCUMENTS

| | | | |
|---|---|---|---|
| 4,501,300 | 2/1985 | Murphy | 138/46 |
| 4,529,399 | 7/1985 | Groshong et al. | 604/53 |
| 4,534,759 | 3/1985 | Trawoger | 604/117 |
| 4,535,818 | 8/1985 | Duncan et al. | 137/846 |
| 4,535,819 | 8/1985 | Atkinson et al. | 137/846 |
| 4,535,820 | 3/1985 | Raines | 137/854 |
| 4,549,879 | 10/1985 | Groshong et al. | 604/247 |
| 4,559,046 | 12/1985 | Groshong et al. | 604/282 |
| 4,566,493 | 1/1986 | Edwards et al. | 137/846 |
| 4,605,395 | 8/1986 | Rose et al. | 604/9 |
| 4,621,654 | 11/1986 | Holter | 137/38 |
| 4,671,796 | 6/1987 | Groshong et al. | 604/247 |
| 4,683,916 | 8/1987 | Raines | 137/854 |
| 4,699,617 | 10/1987 | Moriuchi et al. | 604/246 |
| 4,701,166 | 10/1987 | Groshong et al. | 604/247 |
| 4,737,152 | 4/1988 | Alchas | 604/256 |
| 4,753,640 | 6/1988 | Nichols et al. | 604/247 |
| 4,781,673 | 11/1988 | Watanabe | 604/9 |
| 4,781,674 | 11/1988 | Redmond et al. | 604/9 |
| 4,834,705 | 5/1989 | Vaillancourt | 604/83 |
| 4,883,456 | 11/1989 | Holter | 604/9 |
| 4,885,002 | 12/1989 | Watanabe et al. | 604/9 |
| 4,895,346 | 1/1990 | Steigerwald | 251/149.1 |
| 4,904,236 | 2/1990 | Redmond et al. | 604/9 |
| 4,904,245 | 2/1990 | Chen et al. | 604/248 |
| 4,941,149 | 3/1976 | Mittleman | 137/493 |
| 4,946,448 | 8/1990 | Richmond | 604/247 |
| 4,946,449 | 8/1990 | Davis, Jr. | 604/256 |
| 4,968,294 | 11/1990 | Salama | 600/30 |
| 4,969,870 | 11/1990 | Kramer et al. | 604/51 |
| 5,006,115 | 4/1991 | McDonald | 604/175 |
| 5,009,391 | 4/1991 | Steigerwald | 251/149.1 |

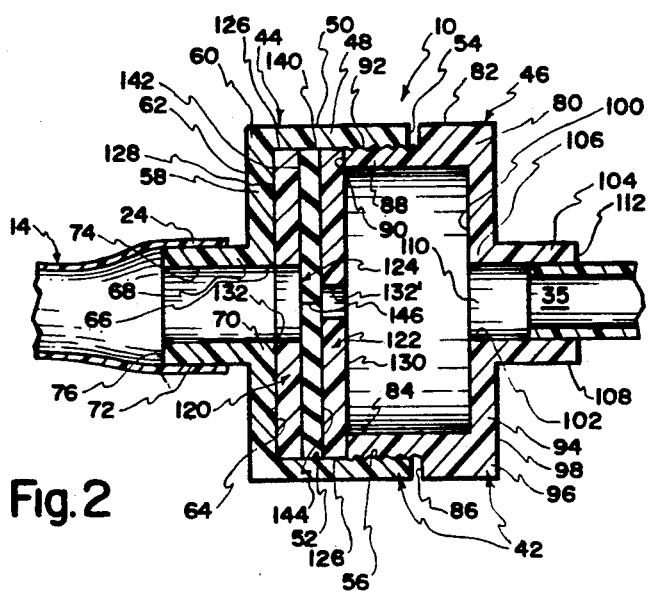
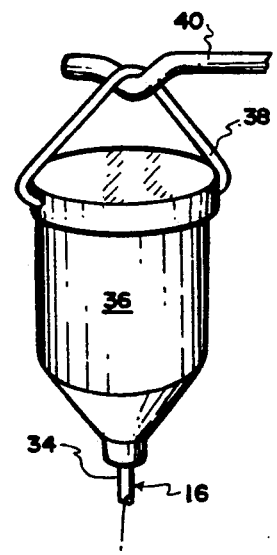
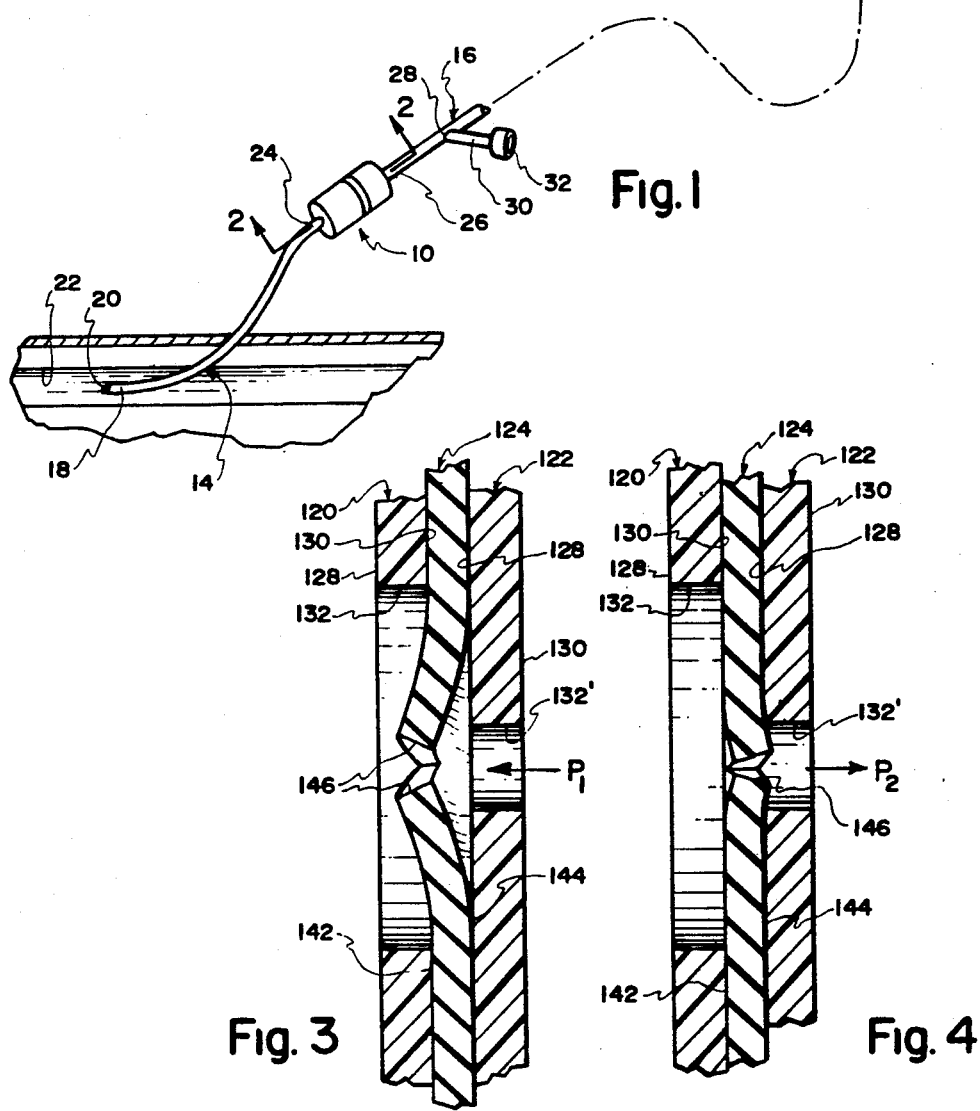
Fig. 2
Fig. 1
Fig. 3
Fig. 4

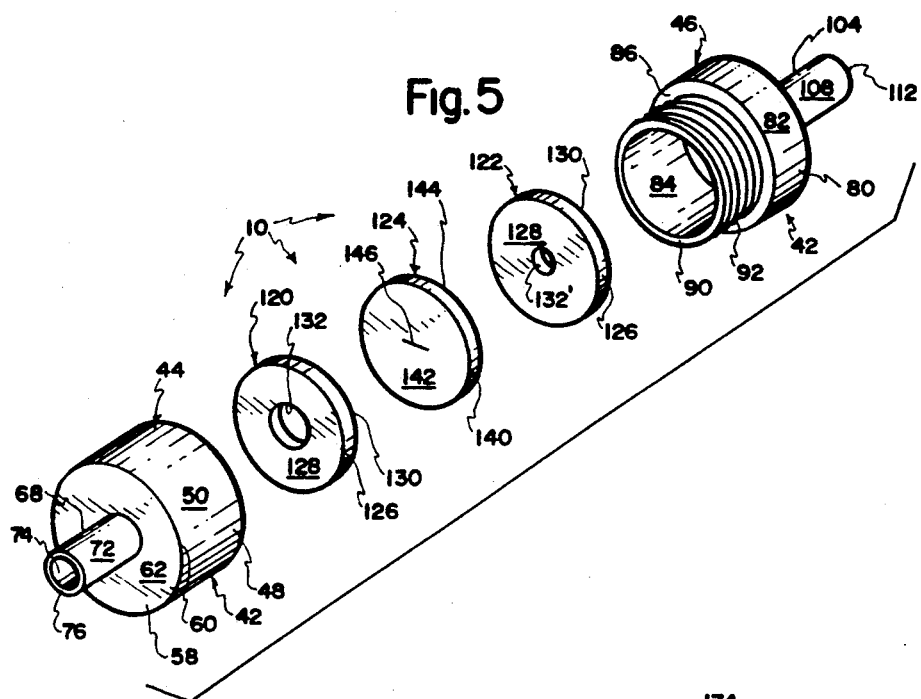
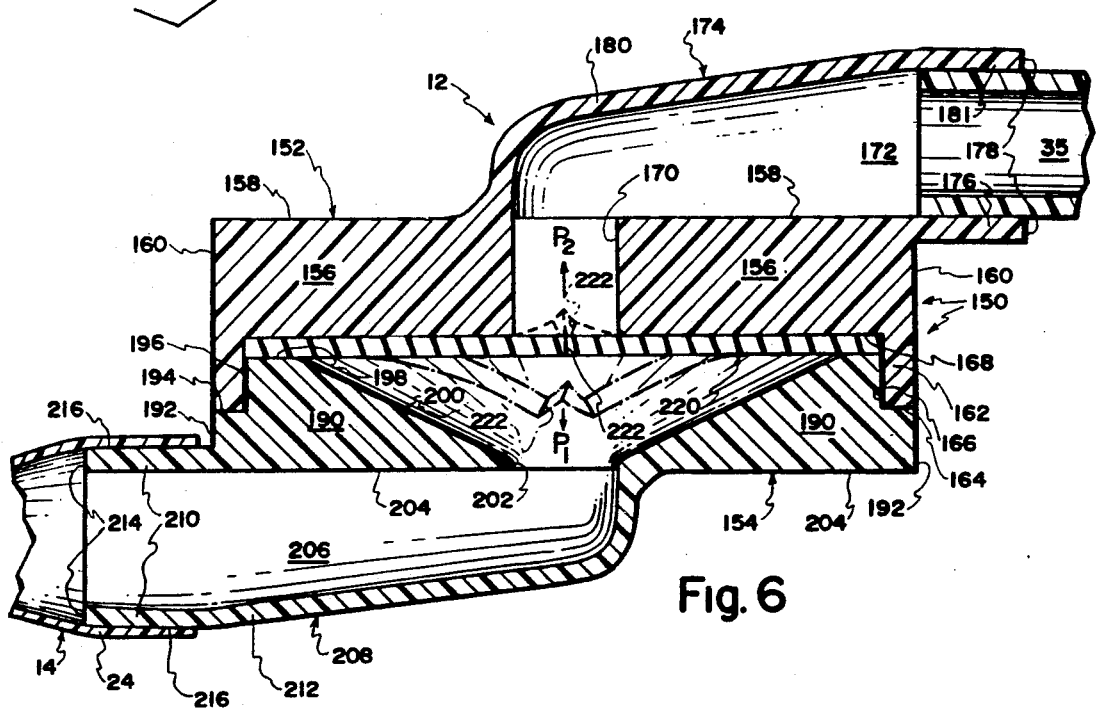

ing cannula, such as a catheter tube or IV needle. However, this approach does not work in a medically-acceptable fashion. Also, the one-way standard valve will not allow blood sampling when the standard one way valve is located between the catheter tube and the sampling site.

TWO-WAY OUTDWELLING SLIT VALVING OF MEDICAL LIQUID FLOW THROUGH A CANNULA AND METHODS

This application is a continuation of our co-pending U.S. patent application Ser. No. 776,927, filed Oct. 15, 1991, now U.S. Pat. No. 5,169,393 which is a continuation of our U.S. patent application Ser. No. 577,941, filed Sep. 4, 1990, now pending.

FIELD OF THE INVENTION

The present invention relates generally to medical liquid flow in a cannula and more particularly to novel structure and methods for outdwelling selective slit valving of medical liquid flow, including bi-direction flow, along a cannula, such as a catheter tube or needle, when the distal end thereof is indwelling in a medical patient.

BACKGROUND AND RELATED ART

It has long been recognized to be medically desirable to intravenously infuse liquid into and to sample blood from a patient. Certain problems have, nevertheless, persisted over the years in the fields of intravenous (IV) infusion and acquisition of blood specimens.

Typically, during delivery of IV solution to the patient through a cannula, such as a catheter tube or IV needle, it is difficult to predict when the supply of IV solution will become exhausted and even more difficult to coordinate availability of nursing personnel with the need to timely disconnect a soon-to-be-dry IV supply from the catheter tube or needle. As a consequence, the distal tip of the cannula sometimes experiences bleed-back and clotting. More specifically, in a conventional IV hook-up to a patient, the flow of IV solution occurs because the force of gravity upon the solution exceeds the blood pressure in the cardiovascular system of the patient. When the supply of IV solution is exhausted, the pressure difference changes so that the cardiovascular pressure prevails, causing blood flow into the IV catheter tube a distance which may vary. Sometimes this blood flow reaches, contaminates and requires replacement of the IV filter. In any event, whether the blood reaches the filter or it does not, the aforesaid blood in the catheter will, within a short time, clot. This risks negligent introduction of the clot into the bloodstream and requires replacement of the IV system, when discovered.

Also, shifting of positions by the patient, as, for example, if the patient raises the venipuncture site above the IV bottle, sometimes causes refluxing or bleedback of blood into the distal end of the cannula. This reflux may or may not reach the IV filter, but in either event causes IV flow to stop which results in clotting within either the cannula, the filter or both.

When and if discovered, both the clotted IV filter and catheter tube are replaced with the accompanying patient trauma and expense. It is bad practice and an unacceptable risk to the patient to force a clot from the catheter tube into the bloodstream, but, due to negligence, this sometimes happens.

It has been proposed that a one-way outdwelling (outside the patient) standard valve be used to prevent undesired blood flow into the distal end of an indwelling cannula, such as a catheter tube or IV needle. However, this approach does not work in a medically-acceptable fashion. Also, the one-way standard valve will not allow blood sampling when the standard one way valve is located between the catheter tube and the sampling site.

BRIEF SUMMARY AND OBJECTS OF THE INVENTION

In brief summary, the present invention overcomes or substantially alleviates the aforesaid problems. The invention comprises novel outdwelling, normally-closed, pressure-responsive medical slit valve liquid flow controls, and related methods, accommodating flow of liquid including, but not limited to, flow of IV solution to the cardiovascular system of a medical patient through a cannula, the distal end of which is indwelling, while preventing bleed-back into and clotting within the cannula and/or IV filter. Thus, cannula and IV filter replacement due to such clotting is obviated. The pressure responsive nature of the slit valve structure prevents the IV system from running dry. Consequently, clots do not form in the cannula and cannot inadvertently be introduced into the bloodstream.

Stated another way, the present invention provides a pressure-sensitive valve that opens in response to the high pressure exerted by a full IV solution bag or bottle but closes as the pressure drops as the bag or bottle empties, which solves or greatly reduces the problem of shutting off the IV flow when the bag or bottle runs dry. The valve opens and achieves adequate flow in response to a predetermined pressure differential, but closes after the pressure drops to a lower predetermined pressure differential.

The present invention accommodates configuration as a two-way valve that opens in either direction at the same or at different pressure differentials, and to allow IV solution in a gravity bag or bottle to flow, shuts off under pressure differential conditions which occur when the IV solution bag or bottle runs dry and yet allows intentional blood sampling across the valve.

Thus, in one presently preferred manifestation of the present invention, the slit valve accommodates bi-directional liquid flow by which both liquid ingress and blood sampling egress proximal of the slit valve are achieved. It is sometimes desirable for a two-way slit valve flow control embodying the present invention to allow distal flexing to open the slit for ingress flow at a relatively low pressure differential and proximal flexing to open the slit for egress flow at a relatively high pressure differential.

In a broad sense, the present invention contemplates provision of an outdwelling, normally closed pressure responsive slit valve by which liquid is selectively communicated to and from a desired internal body site.

Accordingly, it is a primary object of the present invention to overcome or substantially alleviate some if not all of the above-mentioned medical liquid flow control problems.

It is a further significant object to provide a novel outdwelling, normally-closed, pressure-responsive slit valve liquid flow control for use with a medical cannula, and related methods.

Another dominant object is the provision of an outdwelling slit valve structure, and related methods, accommodating flow of liquid, such as IV solution, to the cardiovascular system of a medical patient through a cannula, such as a peripheral catheter tube, a central venous catheter tube, an arterial catheter tube, or an IV needle, while preventing bleed-back into and clotting within the cannula and obviating any resulting need for cannula and IV filter replacement.

A further important object is the provision of novel outdwelling, cardiovascular slit valve structure, and related methods, which prevents an associated IV system from running dry.

An additional principal object of the present invention is the provision of novel outdwelling, two-way slit valve structure, and related methods, for use in achieving selective ingress and egress liquid flow in respect to a desired internal body site of a patient.

A further object of significance is the provision of a novel outdwelling two-way normally closed slit valve, and related methods, in which the slit valve is distally flexed, due to a first predetermined pressure differential, to accommodate intentional fluid flow to a desired internal location in a patient, is closed, due to a second predetermined pressure differential, and is proximally flexed, due to a third pressure differential, to accommodate intentional fluid flow from the internal location in the patient.

Another valuable object is the provision of a novel outdwelling two-way cardiovascular normally closed slit valve, and related methods, in which the slit valve is distally flexed to open a slit for flow to a patient at a relatively low pressure differential across the slit valve and is proximally flexed to open the slit for flow away from the patient at a relatively high pressure differential across the slit valve.

An additional object is the provision of an outdwelling, normally closed slit valve by which liquid is selectively communicated to and from a desired internal body location of a medical patient.

These and other objects and features of the present invention will be apparent from the detailed description taken with reference to the accompanying drawings.

BRIEF DESCRIPTION OF THE DRAWINGS

FIG. 1 is a perspective of one presently preferred outdwelling, two way, normally closed, pressure responsive slit valve flow control, embodying the principles of the present invention, shown in an installed condition;

FIG. 2 is an enlarged cross section taken along lines 2—2 of FIG. 1;

FIG. 3 is an enlarged fragmentary cross section of the slit of the flow control of FIG. 1 flexed open in a distal direction due to pressure differential $P_1$;

FIG. 4 is similar to FIG. 3 but shows the slit flexed open in a proximal direction due to pressure differential $P_2$;

FIG. 5 is an enlarged exploded perspective of the slit valve flow control of FIG. 1; and FIG. 6 is a cross section of a second presently preferred outdwelling, two-way, normally closed, pressure responsive slit valve flow control for a peripheral catheter tube, according to the present invention.

DETAILED DESCRIPTION OF THE ILLUSTRATED EMBODIMENTS

Reference is now made to the drawings wherein like numerals are used to designate like parts throughout. Specifically, FIGS. 1 through 5 illustrate one presently preferred two-way, pressure responsive, outdwelling slit valve flow control mechanism or assembly. FIG. 6 illustrates a second, presently preferred slit valve flow control mechanism or assembly. Both of the illustrated embodiments implement the principles of the present invention, the slit valve flow control assembly of FIGS. 1 through 5 being generally designated 10 and the slit valve flow control mechanism of FIG. 6 being generally designated 12.

Valve assembly 10 is illustrated in FIG. 1 in an "as used" condition, i.e., where the slit valve assembly 10 is interposed between a cannula in the form of a catheter tube, generally designated 14, and an intravenous (IV) tube, generally designated 16. It is to be appreciated that the IV use depicted in FIG. 1 is only exemplary and that the present invention contemplates outdwelling slit valve control for selective delivery of liquid to and from a desired internal location within a medical patient.

The catheter tube 14, illustrated in FIG. 1, may be of any conventional type and is illustrated as having a distal end portion 18 comprising a distal port 20 placed indwelling in the cardiovascular system of a medical patient, namely in the patient's vein 22, as illustrated in FIG. 1. The catheter tube 14 as illustrated in FIGS. 1 and 2 comprises a proximal end portion 24 illustrated, in FIG. 2, as having been force-fit into suitable liquid communication with the slit valve assembly 10, as hereinafter more fully explained.

Likewise, tube 16 may be of any desired type by which liquid is selectively made available to the slit valve assembly 10. IV tube 16 is illustrated as comprising a distal end portion 26 shown as being force-fit into a secured telescopic liquid communicating relationship with the slit valve assembly 10, as hereinafter more fully described. Tube 16 is also illustrated in FIG. 1 as comprising a "Y" site 28, where a hollowed side port 30 emanates. Side port 30 is illustrated as being closed at its proximal end by a conventional elastomeric cap 32, which may be penetrated by a hypodermic needle, for example, and which will reseal upon removal of the needle. Side port 30 and use of a hypodermic syringe is one presently preferred way by which a blood specimen may be removed from or medication introduced into the vein 22 through the catheter 14 and across the slit valve assembly 10 when predetermined pressure differential conditions are brought into play.

FIG. 1 further illustrates IV tube 16 as comprising a proximal end 34 which is illustrated as being connected via a rigid fitting 35 to an IV bottle 36 shown suspended by a bracket 38 upon a cantilevered arm 40, all of which is conventional. Thus, under predetermined pressure differential conditions at slit valve control 10, IV solution in bottle 36 is selectively and controllably introduced into the vein 22 from catheter tube 14 across slit valve 10, responsive to a predetermined hydrostatic head.

With reference to FIGS. 2 through 5, slit valve flow control 10 will now be described. The slit valve flow control 10 comprises a housing, generally designated 42, illustrated as comprising two parts 44 and 46. Housing parts 44 and 46 are preferably formed of shape-retaining synthetic resinous material and are constructed so as to be connected, one to the other, as hereinafter more fully explained. Valve housing part 44 comprises a relatively large annular wall 48, shown as being of substantially uniform thickness and comprising an exposed cylindrical surface 50 and a concealed inner surface 52. Wall 48 terminates in a blunt, transversely oriented edge 54. Interposed between edge 54 and surface 52 are internal threads 56, which form an integral part of wall 48, as illustrated.

Valve housing part 44 also comprises a transversely oriented, radially directed wall 58, which is integral with wall 48 at annular corner 60. Wall 58 is illustrated as having a uniform thickness comprising exposed, external surface 62 and internal surface 64. Wall 48 is interrupted by a centrally disposed aperture 66.

Valve housing part 44 also comprises a distally-extending annular boss in the form of wall 68. Wall 68 is illustrated as having been formed as one piece with, and is, therefore, integral with wall 58 at annular corner 70. Wall 58 is illustrated as being of uniform thickness throughout comprising exterior wall surface 72 and interior wall surface 74. Wall 78 terminates in a transversely oriented blunt edge 76. The diameter of surface 72 is selected, in the illustrated configuration, to be sufficiently greater than the inside diameter of the proximal end 24 of the catheter tube 14 so as to accommodate a satisfactory press-fit relationship between the two, as illustrated in FIG. 2. For such a satisfactory relationship to exist, sufficient compressive force must exist between the proximal end 24 of the catheter tube 14 and the wall 68 so that inadvertent separation of the two does not occur. Where permanent attachment is desired, a suitable bonding agent or adhesive may be applied between the proximal end 24 of the catheter tube 14 and surface 72 of wall 68. The diameter of interior surface 74 of wall 68 is selected to accommodate the desired amount of liquid flow therethrough.

Valve housing portion 46 is illustrated as comprising an annular wall 80, which comprises a smooth exterior cylindrical surface 82 and a smooth interior surface 84, which is substantially longer in an axial direction than is surface 82. Surface 82 merges at a 90° angle with radially-directed, exterior surface 86. Wall surface 86 is illustrated as having a radial dimension essentially half that of the radial thickness of wall 80. Wall segment 80 integrally merges with reduced thickness wall segment 88. The interior surface of wall segment 88 is the previously described surface 84, which merges at a 90° angle with transversely directed blunt edge 90 of wall segment 88. Wall edge surface 90 in turn merges substantially at 90° with threaded surface 92 of wall segment 88. Threads 92 are sized and arranged so as to threadedly match previously described threads 56, accommodating threaded joining of valve housing parts 44 and 46. A suitable adhesive is ordinarily placed between threads 56 and 92 to permanently join housing ports 44 and 46 after the interior components have been correctly placed therein.

Wall segment 80 is formed as one piece and, therefore, integrally joins radially directed wall 94 at annular corner 96. Wall segment 94 is illustrated as being of uniform thickness and as comprising exterior or exposed surface 98 and interior or concealed surface 100. Radially-directed wall 98 is illustrated as being centrally apertured at 102.

Valve housing part 46 is further illustrated as comprising a proximally-directed boss in the form of annular wall 104, which is formed as one piece with and is, therefore, integral with radially directed wall 94 at corner 106. Wall 104 is illustrated as being of uniform thickness comprising external cylindrical wall 108 and internal cylindrical wall 110 having a diameter equal to that of aperture 102. Wall segment 104 terminates in transversely directed blunt edge 112 and has sufficient length and internal diameter to accommodate press-fit acceptance of the rigid male fitting 35 conventionally placed at the distal end 26 of IV tube 16 so as to preclude inadvertent separation.

Three disc-shaped elements are carried within slit valve flow control housing 42 when the two parts 44 and 46 are threadedly secured as illustrated in FIG. 2, namely distal flex control disc 120, proximal flex control disc 122, and central slit diaphragm 124.

Flex control disc 120 is preferably rigid and formed of synthetic resinous materials. Disc 120 is illustrated as comprising a peripheral blunt edge 126 of a disc wall illustrated as being of uniform thickness throughout and comprising distal and proximal flat surfaces 128 and 130, respectively. An aperture 132 is centrally disposed through the disc 120. The diameter of aperture 132 is selected to allow flexing of the diaphragm 124 in a distal direction, as illustrated in FIG. 3, when subjected to a positive differential of a predetermined amount ($P_1$). The resultant pressure $P_1$ is ordinarily primarily caused by the hydrostatic head of the IV solution and is set so that the slit closes while a desired amount of IV solution remains in the tube 16 proximal of the slit. While the diameter of the aperture 132 is illustrated in FIG. 2 as being substantially the same as the diameter of the bore 74, such does not necessarily under all circumstances have to be the case. Also, while the surface defining the aperture 132 is illustrated as being axially disposed, such surfaces may be diagonally or otherwise disposed so long as diaphragm flexing is accommodated at a desired, relatively low pressure differential (diagrammatically illustrated as $P_1$ in FIG. 3). As illustrated in FIG. 2, in the assembled condition, distal surface 128 of disc 120 is contiguous with housing surface 64, while proximal surface 130 is contiguous with the distal surface 142 of slit diaphragm 124.

Proximal flex control disc 122 is similar, as illustrated, to disc 120, except the central aperture 132' of disc 122 is of substantially smaller diameter than the diameter of aperture 132. Since disc 122 is otherwise illustrated as being the same as disc 120, identical numerals have been used and no further description is needed. It is to be noted, however, that the diameter of edge 126 of both disc 120 and disc 122 is just slightly less than the diameter of housing surface 52, to accommodate ease of assembly.

In the assembled condition, as can be seen clearly from FIGS. 2-4, distal surface 128 of flex control disc 122 is contiguous with the proximal surface 144 of the slit diaphragm 124, while a small area of the surface 130 of the flex control disc 122, at the periphery thereof, is contiguous with housing edge 90. It should be readily apparent that the discs 120 and 122 compressively support the slit diaphragm 124 in its radial orientation, except to permit the diaphragm 124 to centrally flex distally and proximally, depending upon pressure differential conditions. Because the diameter of aperture 132' of disc 122 is illustrated as being materially less than the diameter of aperture 132, central flexing of the diaphragm 124 more readily occurs in a distal direction than in a proximal direction. Other configurations, however, are within the scope of the present invention.

In the embodiment of FIGS. 1–5, a relatively high pressure differential (diagrammatically illustrated as $P_2$ in FIG. 4), which flexes the diaphragm 124 proximal into aperture 132' to open slit 146 is required to draw blood proximally through the slit 146 of the diaphragm 124, using, for example, a syringe inserted through elastomeric cap 32 at side port 30 of the IV tube 16. In the embodiment of FIG. 4, a lower pressure differential (diagrammatically illustrated as $P_1$ in FIG. 3) caused in part by the weight of the IV solution in tube 16, which flexes diaphragm 124 distally into the larger aperture 132 to open the slit 146, is required for IV solution to flow.

Slit diaphragm 124 is disc-shaped and is formed of a suitable elastomeric material, such as silicone rubber. Silicone rubber offers the advantage of ease in centrally flexing the diaphragm coupled with good memory characteristics. In an unstressed condition, diaphragm 124 is illustrated (in FIG. 2) as being planar and of uniform thickness, comprising edge 140, the unstressed diameter of which is slightly less than the diameter of housing wall 52. The diaphragm 124 is illustrated as being of uniform thickness comprising distal, radially-directed flat surface 142 and proximal, radially-directed flat surface 144.

Diaphragm 124 comprises a centrally-disposed, normally closed, transversely-directed linear slit 146. Slit 146 is illustrated as uniformly extending from surface 142 to surface 144 and is located so as to be directly aligned with previously mentioned apertures 132 and 132', when placed in the assembled position of FIG. 2. The radial length of slit 146 is selected to accommodate the degree of distal and proximal flexing needed in order to accommodate selective bi-directional liquid flow through the flexed and open slit 146 to introduce, for example, IV solution into the patient under hydrostatic IV pressure or to remove sample blood from the patient under negative pressure or to introduce medication into the bloodstream. In addition to the length of the slit 146, the material used to form the diaphragm 124, the thickness of the diaphragm and the size of apertures 132 and 132' individually and collectively are variables to be set in determining the pressure differentials (diagrammatically illustrated in FIGS. 3 and 4 as $P_1$ and $P_2$) by which the slit 146 is caused to be opened distally and proximally.

It is also to be appreciated that outdwelling fluid control devices according to the present invention can be free standing, for addition to a cannula, such as a catheter or a needle, at the time of use, or can be constructed as a component part of an IV cannula system at the time of manufacture.

Using the slit valve flow control 10 in conjunction with the rest of the system illustrated in FIG. 1, it is to be appreciated that the IV system never runs dry because the flexure in a distal direction required at slit 146 (diagrammatically illustrated as $P_1$ in FIG. 3) ceases to exist while the IV tube 16 is still partially or entirely filled with IV solution. Consequently, it is not possible for bleed-back into and clotting within the catheter tube or other IV cannula to occur. Thus, cannula and/or IV filter replacement due to bleed-back contamination is avoided. When blood sampling occurs via side port 30, the presence of IV solution in the system returns residual blood left in the IV set to the vein 22 immediately following termination of the blood withdrawal cycle. Also, since a blood clot in the cannula, such as catheter tube 14, is not possible, it is correspondingly impossible for a blood clot to be inadvertently discharged from the catheter tube into the vein.

The same essential result may be accomplished using the slit valve flow control mechanism 12, shown in FIG. 6, in lieu of the slit valve flow control assembly 10 of FIGS. 1 through 5. Slit valve flow control mechanism 12 comprises a housing 150 comprising two housing parts, generally designated 152 and 154, respectively.

Housing part 152 comprises a wall 156, illustrated as being of uniform thickness. The wall 156 comprises, as illustrated, an upper surface 158, part of which is exposed and part of which is concealed, and a concealed inside surface 168. Wall 156 also comprises an exposed edge surface 160. A male extension 162 projects downwardly from its integral connection with wall 156. Extension 162 exteriorly comprises surface 160, a blunt edge 164 and internal surface 166. Thus, wall extension 162 in conjunction with wall 156 forms a recess at internal surface 168. Wall 156 and recess at 168 are interrupted by a centrally disposed aperture 170, which extends through wall 156. The diameter of aperture 170 is selected so as to accommodate proximal flexing of an associated diaphragm 220 under a relatively high pressure differential ($P_2$) for blood sampling, consistent with the preceding description.

Valve part 152 comprises a proximal liquid flow passageway 172. Passageway 172 is defined by a liquid flow port wall, generally designated 174. Port wall 174 comprises a lower wall segment 176, shown as having a uniform thickness, which integrally is an extension of wall 156 and terminates in a blunt annular edge 178. Proximal port wall 174 also comprises a curved wall segment 180, which is also integral in part with wall 156 and terminates in the previously mentioned blunt edge 178. Directly adjacent blunt edge 178 is a curved segment 181 of the port wall 174, accommodating press-fit internal receipt of rigid fitting 35 at the distal end 26 of the IV tube 16, in the manner heretofore mentioned. The passageway 172 is sized to accommodate sufficient IV, medication and/or blood sampling flow to accomplish the objectives of the invention.

As is the case with housing part 152, housing part 154 is formed as one piece, preferably of rigid synthetic resinous material. Valve housing part 154 comprises a wall 190 which comprises an exterior edge 192, which merges at 90° with shoulder 194. Shoulder 194 merges at 90° with a reduced diameter surface 196, sized and shaped to press fit against the surface 166. It is presently preferred that surfaces 166 and 196 be permanently secured to each other as illustrated using a suitable adhesive. Surface 196 merges through 90° with an abutment surface 198, which has a relatively short transverse distance. Abutment surface 198 merges with a downwardly convergent recessed surface 200. Surface 200 defines an aperture or orifice 202 at the base thereof which lies in the same plane as the bottom surface 204 of wall 190.

As can be seen by inspection of FIG. 6, wall surface 204 is partly exposed and partly concealed. The concealed portion of surface 204 falls within a liquid flow passageway 206.

Passageway 206 is defined by liquid port wall structure 208, which comprises a thin tube-connecting annular wall extension or lip 210 integral with wall 190, and a curved wall 212, which is also integral with wall 190. Annular wall extension 210 and wall 212 are integral and together terminate in blunt edge 214 at the distal end of the passageway 206. The exterior surface 216 adjacent edge 214 is of such a diameter to accommodate external press-fit connection of the proximal end 24 of the catheter tube 14, in the manner heretofore explained.

From a visual inspection of FIG. 6, it is readily apparent that abutment surface 198 is spaced a predetermined distance from surface 168 of wall 156 when the housing parts 152 and 154 are fully assembled. The space between surfaces 198 and 168 is preferably slightly less than the thickness of a rectangular diaphragm 220. Rectangular diaphragm 120 is illustrated as being of uniform thickness, preferably slightly more than the distance between surfaces 198 and 168 so as to be compression held between surfaces 168 and 198 in the illustrated assembled condition. Diaphragm 220 also comprises a central, normally closed, pressure responsive linear slit 222 which, under predetermined pressure differential conditions selective accommodates bi-directional liquid flow therethrough, flexing in the proximal direction being accommodated by relatively high proximally directed pressure differential $P_2$ and flexing to an open position being accommodated in a distal direction under relatively low distally directed pressure differential $P_1$, such distal flexing being readily accommodated by conical surface 200 of valve housing 154.

In terms of use, since the slit valve flow control mechanism 12 is operatively substantially the same as the already described slit valve flow control mechanism 10, no further operative description is needed.

The invention may be embodied in other specific forms without department from the spirit or essential characteristics thereof. The present embodiments, are, therefore, to be considered in all respects as illustrative and not restrictive, the scope of the invention being indicated by the appended claims rather than by the foregoing description, and all changes which come within the meaning and range of equivalence of the claims are therefore to be embraced therein.

What is claimed and desired to be secured by Letters Patent is:

1. A method of controlling medical liquid flow in a cannula comprising the steps of:
   placing a distal end of the cannula indwelling within an internal body cavity of a medical patient;
   connecting a distal end of an outdwelling slit valve housing directly to a proximal end of the cannula in selective internal medical liquid communication along a predetermined flow path solely due to pressure differential;
   causing a substantially planar normally closed slit diaphragm comprising a centrally disposed slit of predetermined length comprising lips normally disposed in tight edge-to-edge relation and otherwise being impervious to be interposed across the flow path within the housing;
   connecting a proximal end of the outdwelling slit valve housing directly to a distal end of a tube having a proximal end connected to an effluent only source of medical liquid which provides a predetermined distally directed pressure;
   creating a negative pressure at an outdwelling site proximal of the slit diaphragm but remote from the source of a magnitude such that the diaphragm is thereby flexed proximally and the lips of the slit are opened proximally to accommodate unidirectional distal-to-proximal medical liquid flow through the slit from the body cavity of the patient to the remote site.

2. The method according to claim 1 comprising the further step of physically limiting the area of the diaphragm which is permitted to flex proximally to only a predetermined central portion of the total distal area of the diaphragm.

3. The method according to claim 1 comprising the further step of physically altering the pressure differential by altering the negative pressure to cause imposition of an opposite predetermined pressure differential across the diaphragm thereby flexing the diaphragm distally, opening the slit therein and causing proximal-to-distal flow of medical liquid through the slit directly from the effluent only source to the patient.

4. The method according to claim 1 comprising the further step of physically limiting the area of the diaphragm which is permitted to flex distally to only a predetermined central portion of the distal area of the diaphragm.

5. Two-way valve structure for disposition external of a body of a medical patient by which physiological liquid flow to and physiological liquid flow from an internal body cavity site is selectively accomplished, the valve structure comprising:
   housing means comprising proximal liquid ingress and egress flow port means, distal liquid ingress and egress flow port means and a hollow interior defining a single flow path along which physiological liquid selectively flows;
   slit valve means sealingly and transversely disposed within the hollow interior of the housing means and comprising substantially planar diaphragm means of generally uniform thickness in which at least one central normally closed slit comprising edge-to-edge lips is disposed, the diaphragm means further comprising peripheral means imperviously secured to the housing means and solid means interposed between the peripheral means and the lips, the lips being contiguous in tight edge-to-edge relation when the diaphragm means are unflexed, the diaphragm means being contiguous with first and second solid wall means respectively apertured only at a central location aligned with the slit, the central apertures of the first and second solid wall means in combination with said diaphragm means accommodating selective flexing of the lips from a tightly closed to an open position in either direction only when either of first and second predetermined physiological liquid pressure differential thresholds is exceeded, the first solid wall means distal of the diaphragm means controlling at least in part the flex and setting one physiological liquid pressure differential required to open the slit in a distal direction at and solely because of a relatively low differential value and the second solid wall means distal of the diaphragm means controlling at least in part the flex and setting the pressure differential required to open the slit in a proximal direction at and solely because of a relatively high pressure differential value.

6. A method of controlling liquid flow to a hollow cannula comprising the steps of:
   causing a normally closed planar slit diaphragm to be disposed across a flow path in an outdwelling valve structure;
   placing a distal end of the cannula indwelling within a medical patient;
   connecting a distal end of the valve structure to the proximal end of the cannula, thereby placing the flow path of the valve structure in communication with the hollow of the cannula;
   imposing a gravity-caused liquid pressure from a discharge only clean external source of liquid disposed above the patient for gravity liquid infusion upon a proximal side of the diaphragm;
   flexing the diaphragm distally only when the collective liquid pressure upon the diaphragm is distally directed and exceeds a selectively predetermined threshold magnitude; and opening a slit in the diaphragm distally and causing an initial one directional proximal-to-distal flow of the clean liquid only through the slit directly from the discharge only source at least in part under force of gravity to the cannula and thence to the patient;

closing the slit in the diaphragm to stop liquid infusion before flow reverses when the gravity caused pressure is reduced as liquid from the source is spent.

7. A method of controlling uncontaminated medical liquid flow in a cannula comprising the steps of:

placing a distal end of the cannula indwelling within a medical patient;

connecting a hollow distal end of an outdwelling slit valve housing to a proximal end of the cannula in selective internal liquid communication along a predetermined liquid flow path;

causing a normally closed planar slit diaphragm to be securely interposed across the flow path within the housing;

creating a liquid pressure differential across the diaphragm between a pressure internal of the patient and a pressure caused at least in part by gravity operating upon a discharge only uncontaminated liquid source;

flexing the diaphragm distally when the liquid pressure differential is controlled by the pressure of the discharge only source so as to exceed a selectively predetermined threshold pressure without human intervention; and opening distally the slit in the diaphragm only while the flow is proximal-to-distal and causing one way proximal-to-distal flow of uncontaminated liquid through the open slit from the discharge only source directly to the patient.

8. A method of selectively controlling medical liquid flow from a discharge only uncontaminated medical liquid source along tubing directly to a patient, comprising the steps of:

placing a distal end of the tubing indwelling within a medical patient and connecting the proximal end of the tubing to the source;

placing an outdwelling slit valve housing, comprising a planar slit diaphragm, securely between distal and proximal parts of the tubing to create a one-way selectively operable internal liquid communication flow path directly to the patient;

imposing a pressure from within the patient upon a distal side of the diaphragm;

imposing a one-way only liquid pressure having at least a gravity component from the discharge only source upon a proximal portion of a diaphragm securely disposed within the slit valve housing to create a pressure differential which is controlled by the pressure of the discharge only source without human intervention so as to have sufficient selectively predetermined magnitude to flex the diaphragm distally to open a slit in the diaphragm and cause proximal-to-distal flow from the discharge only source through the slit to the patient along the tubing until the magnitude of the pressure differential falls below the selectively predetermined amount;

closing the slit of the diaphragm so as to avoid reflux in response to said lowering of the pressure differential below said selectively predetermined amount.

9. A method of selectively controlling medical liquid flow in tubing comprising the steps of:

placing a distal end of the tubing indwelling within a medical patient;

connecting a distal end of an outdwelling slit valve housing to a proximal end of the tubing in selective internal medical liquid communication along a predetermined flow path;

causing a substantially planar normally closed slit diaphragm comprising a slit of predetermined length comprising lips normally disposed in tight edge-to-edge sealed relation and otherwise being impervious to be interposed across the flow path within the housing;

connecting a one-way source of uncontaminated liquid in one-way flow relationship only to a proximal end of the housing thereby creating a liquid pressure differential, at least due in part to gravity, of at least a selectively predetermined magnitude across an area of the diaphragm in which said slit is disposed to only thereby flex the diaphragm distally to unseal and open the lips of the slit and to accommodate proximal-to-distal uncontaminated medical liquid flow across the open lips of the slit without reflux directly into the tubing and thence directly to the patient, said slit returning to a closed unflexed sealed state when the gravity caused positive liquid pressure differential is positive but falls below the selectively predetermined magnitude.

10. A method of selectively controlling medical liquid flow in tubing comprising the steps of:

placing a distal end of the tubing indwelling within a medical patient;

connecting a distal end of an outdwelling slit valve housing to a proximal end of the tubing in selective internal medical liquid communication along a predetermined flow path;

causing a substantially planar normally closed slit diaphragm comprising a slit of predetermined length comprising lips normally disposed in tight edge-to-edge sealed relation and otherwise being impervious to be interposed across the flow path within the housing;

connecting a one-way source of uncontaminated liquid in one-way flow relationship only to a proximal end of the housing thereby creating a liquid pressure differential, at least due in part to gravity, of at least a selectively predetermined magnitude across an area of the diaphragm in which said slit is disposed to only thereby flex the diaphragm distally and open the lips of the slit and to accommodate proximal-to-distal uncontaminated medical liquid flow across the open lips of the slit directly into the tubing and thence directly to the patient;

altering the liquid pressure differential across the diaphragm causing the diaphragm to flex proximally, physically limiting the area of the diaphragm which is permitted to flex proximally to only a predetermined central portion of the proximal area of the diaphragm and causing distal-to-proximal liquid flow across the diaphragm to a site other than said one-way source.

11. Two-way structure for disposition external of a body of a medical patient by which physiological liquid flow to and physiological liquid flow from an internal body site is selectively accomplished, the valve structure comprising:

housing means comprising proximal liquid ingress and egress flow port means, distal liquid ingress and egress flow port means and a hollow interior defining a single flow path along which physiological liquid flows in a desired direction;

bi-directional displaceable, pressure responsive slit valve means sealingly and transversely disposed within the hollow interior of the housing means and comprising substantially planar diaphragm means of generally uniform thickness in which at least one central normally closed slit comprising edge-to-edge lips is disposed, the diaphragm means further comprising peripheral means imperviously secured to the housing means and solid means interposed between the peripheral means and the lips, the lips being contiguous in tight edge-to-edge relation when the diaphragm means are unflexed, the slit valve means further comprising first and second solid wall means respectively apertured only at a central location aligned with the slit, the first and second solid wall means being contiguous with the diaphragm means other than at the central aperture of each of said first and second solid wall means when the diaphragm means are unflexed and which comprise peripheral edges also secured to the housing means and control apertures in combination with said diaphragm means accommodating selective flexing of the lips from a tightly closed to an open position in either direction only when either of first and second predetermined physiological liquid pressure differential thresholds is exceeded, the first solid wall means distal of the diaphragm means controlling at least in part the flex and setting one physiological liquid pressure differential required to open the slit in a distal direction at a relatively low differential value and the second solid wall means proximal of the diaphragm means controlling at least in part the flex and setting the pressure differential required to open the slit in a proximal direction at a relatively high differential value.

12. Two-way physiological valve structure for disposition external of a body of a medical patient, the valve structure comprising:

housing means comprising proximal physiological liquid ingress and egress flow port means, distal physiological liquid ingress and egress flow port means and a hollow interior defining a single flow path along which physiological liquid entering the port means selectively flows in a desired direction;

bi-directional displaceable, pressure-responsive slit valve means transversely disposed within the hollow interior of the housing means and comprising peripheral means imperviously secured at the housing means, the slit valve means further comprising normally closed slit means with memory comprising opposed lips with contiguous opposed edge held sealingly and alignedly together by said memory only when physiological liquid pressure differential across the slit valve means is within a predetermined range, the edges separating to open the slit valve means only when physiological liquid differential pressure is above or below the predetermined range to accommodate proximal and distal liquid flow respectively along the single flow path in a single direction during liquid egress flow and in the opposite direction during liquid ingress flow;

means apertured only at the center thereof contiguously associated with slit valve means and also imperviously secured at the housing means for selectively determining in combination with said slit valve means said predetermined range, said range determining means comprising a central aperture and being contiguously juxtaposed said slit valve means adjacent to said central aperture.

13. Valve structure according to claim 12 wherein the slit means comprise an elastomeric diaphragm comprising at least one slit, the diaphragm being flexed to separate the lip edges only when the physiological liquid pressure differential is above and below the range.

14. Valve structure according to claim 13, wherein the diaphragm is flat and of generally uniform thickness.

15. Valve structure according to claim 13 wherein the diaphragm comprises an elastomeric disc.

16. Valve structure according to claim 13 wherein the diaphragm is rectangularly shaped.

17. Valve structure according to claim 12 wherein the housing means comprise at least two parts and releasible fastening means holding the two parts together.

18. Valve structure according to claim 17 wherein the two parts are fastened together by threaded connectors.

19. A cardiovascular assembly comprising:

first tubing means comprising a hollow interior for placement, at a distal end thereof, in a cardiovascular system of a patient;

a source of liquid disposed external of and above the patient by which a first always positive liquid pressure caused at least in part by gravity is created in the assembly and from which an essentially uncontaminated flow of the liquid is provided directly to the patient without human manipulation;

second tubing means comprising a hollow interior and distal and proximal ends disposed external of the patient, the hollow interior of the second tubing means at the proximal end being in direct communication with the source liquid at the first liquid pressure;

two-way valve structure without selectively settable parts contiguously and directly interposed between the distal end of the second tubing means and the first tubing means at a proximal end thereof external of the patient, a proximal part of the two-way valve structure being in direct communication with the interior of the second tubing means at the distal end thereof, the source liquid therein and the first liquid pressure and a distal part of the two-way valve structure being only and directly in communication with the hollow interior of the first tubing means at a proximal end thereof and a second cardiovascular pressure therein when said first tubing means are disposed in liquid communication with the cardiovascular system of the patient;

the second tubing means further comprising means for selectively applying a third pressure across said two-way valve structure; and the two-way valve structure comprising centrally interior normally closed bi-directionally pressure-responsive slit valve means, the slit valve means being imperviously secure at its periphery and selectively accommodating only unidirectional flow of a predetermined quantity of liquid across the valve structure directly between the first and second tubing means only directly along selectively openable/closeable centrally disposed flow path means only in a proximal to distal direction flow of said predetermined quantity of liquid to the patient without human manipulation only when the first pressure exceeds the second by a predetermined magnitude and the third pressure is not being imposed, flow in a distal to proximal direction across the two-way valve structure only when the third pressure controls and reaches a predetermined amount.

20. An assembly according to claim 19 wherein the slit valve means comprise an elastomeric diaphragm and the centrally disposed flow path means comprise a central slit having opposed lips whereby the lips of the slit are flexed open in either direction only when the difference in the first and second pressures is above a predetermined threshold value.

21. An assembly according to claim 20 wherein the diaphragm comprises an elastomeric disc.

22. An assembly according to claim 20 wherein the diaphragm is rectangularly shaped.

23. An assembly according to claim 19 wherein the two-way valve structure comprises hollow housing means comprising means which imperviously secure the slit valve means at the periphery thereof.

24. An assembly according to claim 23 wherein the hollow housing means comprise at least two parts fastened together.

* * * * *